United States Patent [19]

Tyler

[11] Patent Number: 5,024,654
[45] Date of Patent: Jun. 18, 1991

[54] INSULATED INFUSION AND ASPIRATION PROBE

[75] Inventor: Hugh J. Tyler, Santa Ana, Calif.

[73] Assignee: Alcon Surgical, Inc., Fort Worth, Tex.

[21] Appl. No.: 415,904

[22] Filed: Oct. 2, 1989

[51] Int. Cl.$^5$ ............................................. A61M 3/00
[52] U.S. Cl. ...................................... 604/43; 604/28; 604/35; 604/284
[58] Field of Search ................... 604/22.27, 28, 34–36, 604/39, 43, 93–94, 96–97, 99, 100, 264, 280, 282, 284

[56] References Cited

U.S. PATENT DOCUMENTS

| | | | |
|---|---|---|---|
| 2,257,369 | 9/1941 | Davis | 604/43 |
| 2,393,002 | 1/1946 | Smith | 604/43 |
| 2,492,384 | 12/1949 | Kaslow | 604/280 |
| 3,512,517 | 5/1970 | Kadish et al. | 604/27 X |
| 4,553,957 | 11/1985 | Williams et al. | 604/43 |
| 4,819,664 | 4/1989 | Nazari | 128/207.5 |

*Primary Examiner*—C. Fred Rosenbaum
*Assistant Examiner*—Corrine Maglione
*Attorney, Agent, or Firm*—Neuman, Williams, Anderson & Olson

[57] ABSTRACT

A surgical instrument is provided which has two concentric transfer tubes: an outer tube and an inner tube. One tube is used for aspiration of fluid, the other for infusion of fluid. The concentric tubing section has proximal and distal ends, the distal end being tapered and having openings for simultaneous aspiration and infusion eye fluid. On the proximal end, the inner transfer tube extends a proximal length greater than the outer transfer tube. The concentric inner and outer transfer tubes are both connected to independent supply tubes. The proximal end of the inner transfer tube, being longer than the outer transfer tube, pierces and protrudes through the wall of the flexible fluid tube connected to the proximal end of the outer tube. This protrusion provides a place on the inner transfer tube for its own independent connection to a supply tube. The tubing assembly is contained within and supported by an elongated, generally tubular housing. This housing insulates the tubes by means of an air space substantially along the full length of the housing.

9 Claims, 2 Drawing Sheets

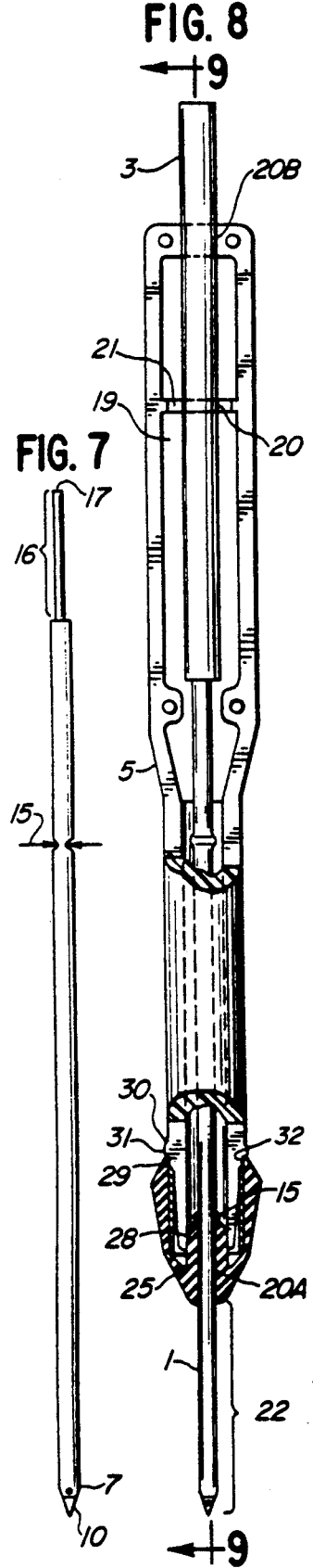
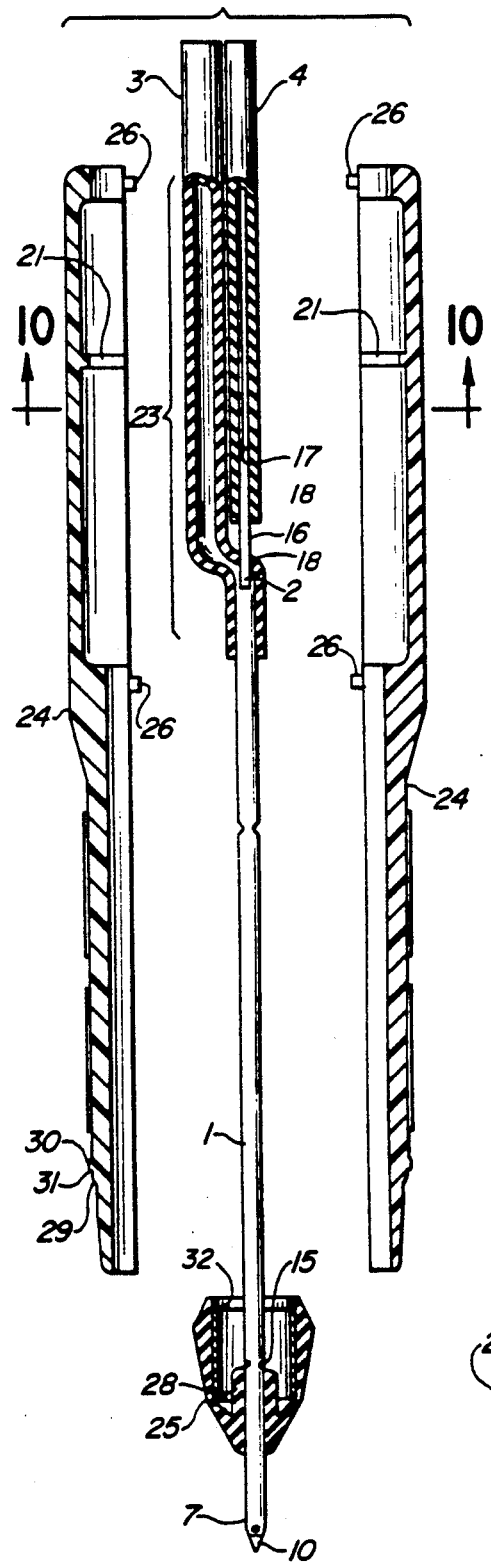
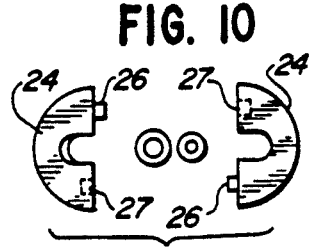

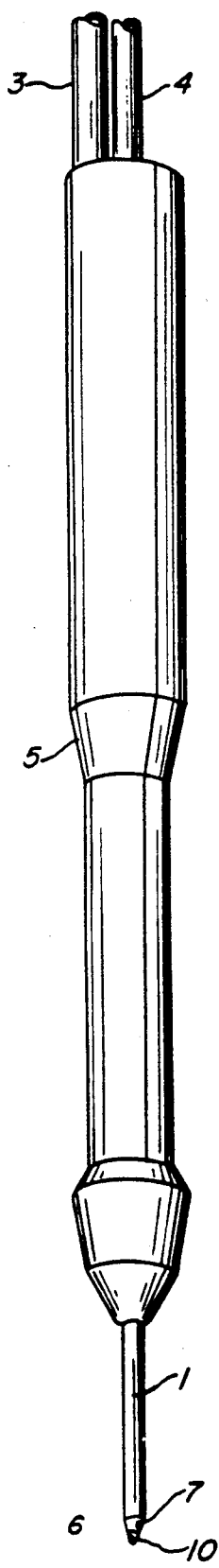
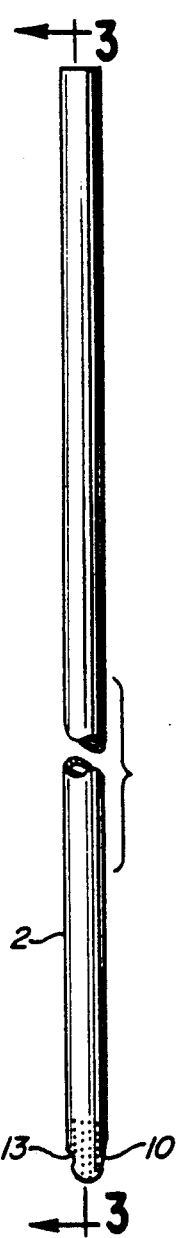
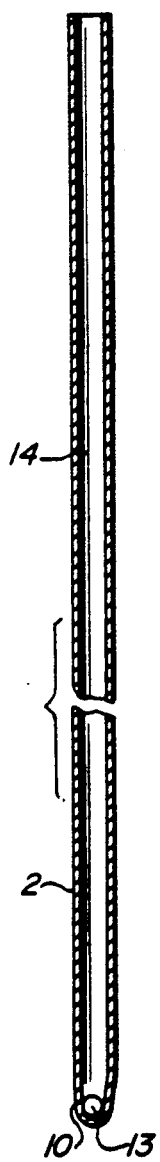
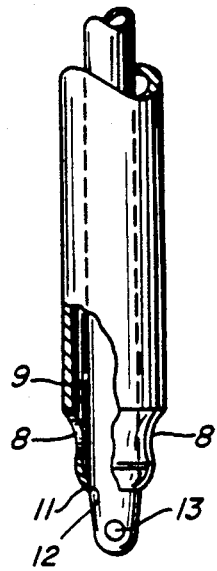
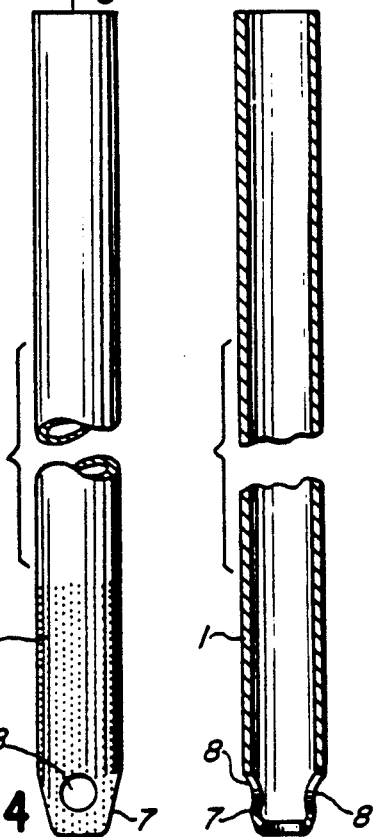

INSULATED INFUSION AND ASPIRATION PROBE

BACKGROUND OF THE INVENTION

1. Field Of The Invention

This invention relates generally to a surgical instrument and its assembly and more particularly concerns a surgical instrument used for removing particles and fluid from an eye during cataract surgery while also infusing replacement fluid.

2. Brief Description Of The Prior Art

Cataract surgery on the human eye requires, in part, that the eye lens capsule be cleaned of particles. This task is accomplished by aspirating particulate-laden fluid from the interior of the eye and replacing it with clean fluid. It is necessary to perform the aspiration and infusion of fluid simultaneously in order to maintain appropriate internal pressure and volume of the lens cavity.

Such a fluid exchange is typically performed by a small, hand-held probe which is inserted in the eye through an incision, and which includes two rigid transfer tubes, one tube for fluid removal and the other for fluid infusion. These two transfer tubes are connected to two fluid supply tubes, one of which provides infusion fluid, and the other is connected to a vacuum source. Many prior art ophthalmic probes for infusing and aspirating fluid utilize a concentric tube configuration.

Precision manufacturing and assembly of such instruments are expensive, and a probe with several complex parts is likely to be costly. Conventional probes, for example, ordinarily use specially shaped ducting components to perform the function of directing fluid flow from two side-by-side tubes into a probe tip having a concentric tube flow configuration. Martinez, U.S. Pat. No. 4,652,255 is exemplary, disclosing a device where infusion fluid is routed from a side tube into an annular reservoir in the handle from where it flows through a concentric tube to the eye. The Martinez device includes several small and rigid components which must be precision manufactured in order to meet the demands of ophthalmic surgery.

It is desirable in such a probe to prevent the warming of the infusion fluid, because lower fluid temperature minimizes the chance of illumination light damage to the eye during the procedure. Advanced technology surgery systems cool the fluid for this reason. Yet some ophthalmic probes leave the flow tubes exposed, susceptible to contact with a surgeon's hand during the procedure. See for example, Grandon, U.S. Pat. No. 4,578,058. Other probes disclosed in the prior art provide a handle which encloses the tubes; however, there is no disclosure of any means specifically to insulate the infusing fluid. See for example, Woods, U.S. Pat. No. 4,652,255, and Reimels, U.S. Pat. No. 4,705,500, which disclose solid handles in direct contact with the tubes.

In the Martinez device, where the handle body doubles as fluid reservoir, the fluid flows through a cavity formed by the housing and is then infused into the eye through a concentric channel. With this design, the relatively large quantity of fluid in the handle adds weight and subjects the fluid to warming by the surgeon's hand.

Although these prior teachings show that a hand-held ophthalmic infusion/aspiration probe is effective when comprised of concentric tubes, none addresses the problem of keeping the fluid cool while also maintaining light weight and low cost by the use of few, simple components.

In accordance with the foregoing, it is a general object of this invention to provide a improved fluid infusion and aspiration probe for use in removing particles from the eye during cataract surgery.

A related object is to provide such a surgical probe which has relatively few parts, is simple in design, and is inexpensive to manufacture.

A more specific object of the invention is to provide a simple and effective method of connecting two separate supply tubes to the separate concentric fluid transfer channels of such a probe.

Another object of the invention is to provide an infusion/aspiration probe which will hold only a small amount of fluid, thereby being lightweight and responsive.

Another object of the invention is to provide a surgical instrument which insulates the infusing eye fluid from the warming effects of a surgeon's hand.

It is a further object of the invention to provide a simple and effective means to relatively fix two concentric tubes of a surgical instrument.

Other objects and advantages of the present invention will be apparent to those skilled in this art from the following description and the appended claims.

SUMMARY OF THE INVENTION

The present invention is a surgical instrument, specifically a probe, which includes an outer transfer tube having a proximal end and a distal end; an inner transfer tube housed within and concentric to the outer tube, the inner tube having a proximal end and a distal end which has a segment extending proximally beyond the proximal end of the outer transfer tube; a first supply tube connected to the proximal end of the outer transfer tube and having the proximally extending segment of the inner transfer tube extending through the wall of the first supply tube; and, a second supply tube connected to the proximal end of the inner tube. In one preferred form the probe has an elongated, generally tubular housing which has means for thermally insulating the supply tubes and the transfer tubes from the walls the housing. The probe also preferably has a simple, economical fixing means, i.e., a crimp, for preventing axial and radial movement of the inner transfer tube relative to the outer transfer tube.

The basic structure of the probe of the invention, like that of other commonly used surgical instruments, is a section of concentric tubing comprising an inner transfer tube and an outer transfer tube, both having proximal and distal ends. Because the fluid flows only through small diameter concentric tubing, there is a minimal amount of fluid in the probe, making it lightweight and responsive. The distal end is usually tapered to provide ease of insertion through an incision.

In the present invention, the distal end of the outer transfer tube is tapered in shape, but open at the tip. Proximal to this open tip, there is at least one opening in the wall of the outer transfer tube. The inner transfer tube, which is housed within the outer transfer tube, is prevented from moving axially or radially relative to the outer tube by means of a crimp in the two tubes. This crimp is deep enough to deform both the inner and outer transfer tubes, yet slight enough to make the inner transfer tube only slightly oval in cross-sectional shape. It has been found that flow is not significantly restricted by the crimp through either the inner or outer tube. Crimping the tubes is a novel, effective, and inexpensive means for fixing the position of these fluid transfer tubes relative to one another, and it requires no additional parts.

The inner transfer tube has a tapered closed tip, the outer surface of which engages the outer transfer tube at the inner surface of the outer tube's open tip, forming a seal between them. This seal prevents flow from the tip of the outer tube except through the one or more openings in its wall. There is an opening in the inner tube proximal to its closed tip, but distal to the engagement.

The proximal ends of the concentric transfer tubes are open. Supply lines are connected to the inner and outer transfer tubes at their proximal ends. Since there is no supply communication between the inner and outer transfer tubes, one fluid tube can provide pressurized fluid to one transfer tube while the other supply tube provides suction to the other transfer tube.

A segment of the inner tube extends a greater proximal distance than the outer tube. This segment provides a novel, inexpensive, and simple means to connect supply lines to the transfer tubes. The proximally extending segment of the inner transfer tube pierces and protrudes through the wall of a first supply tube connected to the outer transfer tube. The portion of the inner tube which protrudes through the wall of the first fluid tube is connected to a second supply tube, which can be independent of the first. This means of directing flow from two tubes into a concentric configuration requires fewer parts than used by prior devices, and demands less precision in manufacturing and assembly, since in the preferred embodiment the supply tubes are formed of a flexible material.

Excepting for a length on the distal end of the concentric transfer tubes, the transfer tubes and supply tubes are contained within and supported by an elongated, generally tubular housing. There is an air space between the wall of the housing and the tubes substantially throughout length of the housing. This air space provides a thermal insulation means between the tubing apparatus and the housing wall. Insulation is critical to maintaining the temperature of the cooled infusing fluid.

Moreover, since there is a very small volume of fluid contained within the probe, it is light and maneuverable, which reduces surgeon fatigue and assists in accurate placement within the eye.

The overall design thus uses a minimum number of parts. The parts used are simple, and they require no special expensive manufacturing or assembly methods such as brazing or bonding.

BRIEF DESCRIPTION OF THE DRAWINGS

FIG. 1 is a plan view of an assembled ophthalmic fluid infusion/aspiration probe in accordance with the present invention.

FIG. 2 is a fragmentary plan view of the inner transfer tube.

FIG. 3 is a fragmentary sectional view of the inner transfer tube taken along line 3—3 of FIG. 2.

FIG. 4 is an enlarged fragmentary view of the outer transfer tube.

FIG. 5 is a fragmentary sectional view of the outer tube taken along line 5—5 of FIG. 4.

FIG. 6 is a partial sectional view of the distal tip of the concentric transfer tubes.

FIG. 7 is a plan view of the inner and outer transfer tubes together in the concentric configuration, secured by the crimp.

FIG. 8 is a partial sectional top view of the probe assembly.

FIG. 9 is a partially exploded, partially sectional view of the probe assembly, taken along line 9—9 of FIG. 8.

FIG. 10 is a cross-sectional, exploded view of the probe assembly, taken along line 10—10 of FIG. 9.

It should be understood that the drawings are not necessarily to scale and that the embodiments are sometimes illustrated by graphic symbols, phantom lines, diagrammatic representations and fragmentary views. In certain instances, details difficult to perceive may have been omitted. It should be understood, of course, that the invention is not necessarily limited to the particular embodiments illustrated herein.

DETAILED DESCRIPTION

A surgical instrument according to the present invention which provides a means for infusing and aspirating fluid from an eye during ophthalmic surgery which is shown assembled in the preferred embodiment by FIG. 1. It includes as its basic components an outer transfer tube 1, an inner transfer tube 2, and supply tubes 3 and 4, all partially encased by a housing 5. Being a simple device, the probe is inexpensively manufactured and is disposable.

The inner and outer transfer tubes 1 and 2 are joined in a concentric arrangement (see FIGS. 6 and 7), the distal tip 6 of which (see FIG. 1) is manually inserted through an incision in the eye by the surgeon. As shown in more detail in FIGS. 4 and 5, the distal tip 7 of the outer tube is open, tapered, and has at least one opening 8 in its wall proximal and adjacent to its open, tapered tip. Preferably, there are two openings 8 in the wall, each being circular and opposing the other. These openings allow fluid flow communication between an outer annular channel 9 and the eye cavity.

It can be seen in FIG. 6 that the inner transfer tube 2 fits within the outer tube 1 so as to form annular channel 9 defined by the volume between the outer surface of the inner tube 2 and the inner surface of outer tube 1. And, as shown there, the distal tip portion 10 of the inner tube 2 is tapered and engages outer tube 1 in a complementary manner such that a seal is formed between them at the engagement 11. The engagement 11 is formed preferably where an annular, beveled edge 12 along the inside of the open tip 7 of the outer transfer tube 1 abuts the tapered distal tip 10 of the inner tube 2. There is at least one opening 13 in the tapered portion of the inner tube 2 located in the inner tube's wall distal to the engagement 11, and the opening is preferably circular in shape. This opening provides flow communication between the flow channel 14 within the inner tube and the eye cavity. Since there are two channels for flow provided by the tubes 1 and 2, aspiration of fluid from the eye may be performed by one channel while the other simultaneously infuses fluid into the eye.

One feature of the present invention is a crimp 15 which holds the inner transfer tube 2 and outer transfer tube 1 fixed in position relative to each other. This crimp is preferably located nearer to the distal end of outer tube 1, since the crimp will also then serve to prevent the concentric transfer tubes 1 and 2 from being pulled out of the housing. (See FIGS. 7 and 9 for a preferred crimp location.) Optionally, and regardless of the position of the crimp 15, a bonding material, such as RTV (room temperature vulcanizing) rubber, may be used to lock the needle assembly to the nose piece 25.

The crimp 15 is of sufficient depth that it deforms both the outer tube 1 and the inner tube 2 in an interlocking relation; however the crimp is slight enough that flow through the concentric channels and is not significantly restricted. The crimping should be performed by a precise, controlled operation to obtain a sufficient crimp while not overcrimping. The use of a crimp to secure the concentric transfer tubes together eliminates additional parts which otherwise would be required to perform the same function.

Attention is drawn to the next feature of the invention which is a means to connect the concentric transfer tubes to the two separate supply lines 3 and 4. According to the present invention, the concentric transfer tubes 1 and 2 are connected directly to the fluid supply lines 3 and 4 in a simple, inexpensive manner. To accommodate this, the inner transfer tube 2 is longer than the outer transfer tube 1; the inner tube 2 extending a proximal length farther than the outer tube, forming a segment 16. The supply tubes are preferably made of commonly available flexible rubber or plastic tubing suitable for surgical applications. The first supply tube 3 is frictionally connected to the outer transfer tube 1 by simply inserting the transfer tube 1 into the end of the supply tube 3; however, a portion of segment 16 of the inner transfer tube 2 pierces and protrudes through the wall of this first supply tube 3. The supply tubes are made preferably of such rubber or plastic that the proximal tip 17 of the inner transfer tube may pierce the first supply tube 3 during assembly and form a seal at the protrusion 18. Both vinyl and silicone tubing have been found to perform adequately. Optionally, a solvent or sealant may be applied to the pierced area of fluid tube to provide added protection from leakage. One suitable sealant is RTV rubber. After the first supply tube 3 is connected to outer transfer tube 1 in the described manner, the protruding section of the segment is connected to the second supply tube 4 in the same manner as outer transfer tube 1 is connected to first supply tube 3.

In addition to the particular configuration depicted in FIGS. 8 and 9, one may alternatively utilize a shorter concentric needle assembly and longer supply tubes. Indeed, in a properly configured housing, the point of connection between the transfer tubes and the supply tubes may be within the nose piece. The advantage of such a configuration is that a shorter needle assembly is less costly and permits improved fluid flow through the probe.

The present invention is also concerned with insulating the tubing assembly, and therefore the fluid, from the heat of the surgeon's hand. As explained above, the infusing fluid is cooled before it flows to the hand held probe.

The probe of the present invention provides a housing 5 having an air space which acts as ann insulating means to minimize heat transfer to the cooled fluid. In the preferred embodiment depicted in the drawings, particularly FIGS. 8 and 9, the housing 5 is elongated and generally tubular. It supports and substantially encases the tubing assembly. The housing does not contact the surface of the tubes along a substantial portion of the housing's length, providing an air space 19 between the inner surface of the housing wall and the outer surface of the outer transfer tube 1. This air space 19 insulates the tubing wall from the housing wall. The space may be simply an air gap or it may optionally contain some other insulating material. The tubing surface preferably contacts the housing surface only at the minimum number points necessary to provide support and secure positioning with respect to the probe as a whole. In the preferred embodiment (see FIGS. 8-10), these locations are at each end of the housing, i.e., circular passage 20A at the nose piece 25 through which the concentric transfer tubes extend, and oblong passage 20B at the proximal end of housing 5 through which supply tubes 3 and 4 extend. Ordinarily, the frictional engagement between supply tubes 3 and 4, and passage 20B is sufficient to maintain the concentric needle and tube assembly in proper position within the housing.

For maintaining the fluid's low temperature, it is highly desirable that a minimum amount of fluid is in the probe at any time and, in the probe of the present invention, the volume of fluid is limited to that contained in the concentric tubes. The small amount of fluid in the tubes has the added advantage of making the probe lightweight and responsive in the hand of the surgeon.

The proximal end of the housing preferably extends beyond the proximal end of the inner concentric tube, thereby encasing a short length 23 of the flexible supply tubes beyond their connections to the transfer tubes.

The housing 5 consists of more than one piece so that it may be easily assembled. Preferably, the housing comprises two identical shells 24 with an annular nose piece 25 on its distal end. Each shell is semicircular in cross-section (see FIG. 10) so that when the two are assembled, they form the body of the elongated, generally tubular housing 5. As shown in FIGS. 8 and 9, the housing 5 includes an interior circular wall 21. The shell halves 24 are connected together by tapered pins 26 and holes 27. The shells 24 are pressed together, forcing the pins 26 into the holes 27. The maximum diameter of the pins is slightly larger than the diameter of the holes, causing an interference fit. The annular nose piece 25 slides over the distal tip portion of the concentric tubes and snap fits to the assembled shells. The shells 24 do not contact the transfer tubes at the shells' distal ends, as does the nose piece 25. Rather, the nose piece 25 has a sleeve which contacts and slides over the outer transfer tube 1 and also fits into the distal end of the shell assembly, maintaining the centered radial position of the concentric transfer tubes relative to the shells. The body of the nose piece 25 is generally hollow, with the annular wall sweeping axially in the proximal direction from the distal end of the sleeve.

The snap fit connection of the nose piece 25 is provided by two annular ridges 29 and 30 on the perimeter of the outer surface of the shells 24 near the shells' distal end, but proximal to the shells' distal ends, in cooperation with an annular lip 32 on the interior of nose piece 25. The first ridge 29 is immediately distal to the second ridge 30, which is larger in radius. There is a narrow channel 31 which separates the ridges. The nose piece 25 is connected to the housing assembly by pressing the nose piece body and the shell assembly together. This forces the annular lip 32 of the nose piece 25 to slide over the first ridge 29 until it comes into contact with the second ridge 30 which stops the nosepiece in proper position. Thus, the nose piece snap fits and holds the distal ends of the shells 24 together.

From the foregoing description and examples, it is apparent that the objects of the present invention have been achieved. While only certain embodiments have been set forth, alternative embodiments and various modifications will be apparent to those skilled in the art. These and other alternatives and modifications are considered equivalents and within the spirit and scope of the present invention.

What is claimed is:

1. A surgical instrument comprising:
   (a) an outer transfer tube having a proximal end and a distal end;
   (b) an inner transfer tube housed within and concentric to said outer tube, said inner tube having a proximal end and a distal end, and having a segment extending proximally beyond the proximal end of said outer transfer tube;
   (c) a first supply tube connected to said proximal end of said outer transfer tube and having said proximally extending segment of said inner transfer tube extending through the wall of said first supply tube;
   (d) a second supply tube connected to said proximal end of said inner tube; and,
   (e) an elongated, generally tubular housing, said housing contacting and supporting said tubes at the ends of said housing and substantially containing said outer transfer tube, said inner transfer tube, and said first and second supply tubes, the walls of said housing being spaced from said transfer tubes and said supply tubes substantially throughout the length of said housing to minimize heat transfer from said housing to said tubes.

2. A surgical instrument according to claim 1 having at least one protuberance on the interior of said outer transfer tube and at least one complemental recess on the exterior of said inner transfer tube for preventing axial and radical movement of said inner transfer tube relative to said outer transfer tube.

3. A surgical instrument according to claim 2 wherein said fixing means is a crimp in said outer tube and said inner tube.

4. A surgical instrument comprising:
   (a) an outer transfer tube having a proximal end and a tapered, open, distal end, said distal end having at least one opening formed in the wall thereof adjacent said open distal end;
   (b) an inner transfer tube housed within and concentric to said outer tube, said inner tube having a proximal end and a tapered distal end, said distal end having a closed tip portion, and said inner tube having at least one opening formed in the wall thereof adjacent said closed tip portion, and having a segment extending proximally beyond the proximal end of said outer transfer tube,
   an exterior portion of said tapered end of said inner tube engaging said open, distal, tapered end of said outer transfer tube, whereby said engagement between said tubes forms a seal proximal to said at least one opening of said inner transfer tube;
   (c) a first supply tube connected to said proximal end of said outer transfer tube and having said proximally extending segment of said inner transfer tube extending through the wall of said first supply tube,
   (d) a second supply tube connected to said proximal end of said inner tube; and
   (e) an elongated, generally tubular housing, said housing contracting and supporting said tubes at the ends of said housing and substantially contacting said outer transfer tube, said inner transfer tube, and said first and second supply tubes, the walls of said housing being spaced from said transfer tubes and said supply tubes substantially throughout the length of said housing to minimize heat transfer from said housing to said tubes.

5. A surgical instrument according to claim 4 wherein said fixing means comprises at least one protuberance on the interior of said outer transfer tube and at least one complemental recess on the exterior of said inner transfer tube.

6. A surgical instrument according to claim 4 in which said supply tubes are formed of a flexible material.

7. A method of manufacturing a surgical instrument having
   (a) an outer tube having a proximal end and a distal end;
   (b) an inner transfer tube housing within and concentric to said outer tube, said inner tube having a proximal end and a distal end, and having a segment extending proximally beyond the proximal end of said outer transfer tube;
   (c) a first supply tube connected to said proximal end of said outer transfer tube and having said proximally extending segment of said inner transfer tube extending through the wall of said first supply tube;
   (d) a second supply tube connected to said proximal end of said inner tube; and
   (e) an elongated, generally tubular housing, said housing contacting and supporting said tubes at the ends of said housing and substantially containing said outer transfer tube, said inner transfer tube, and said first and second supply tubes, the walls of said housing being spaced from said transfer tubes and said supply tubes substantially throughout the length of said housing to minimize heat transfer from said housing to said tubes,
   said method comprising the steps of (1) inserting said proximal end of said outer transfer tube and said proximal end of said inner transfer tube into one end of said first supply tube; (2) piercing the wall of said first supply tube with said proximal end of said inner transfer tube whereby substantially the full length of said proximally extending segment extends outside said first supply tube; (3) inserting said proximally extending segment of said inner transfer tube into one end of said second supply tube; and, (4) attaching said housing onto said instrument.

8. A method of performing a surgical procedure comprising the steps of (1) forming an incision in a fluid-containing body, (2) inserting an instrument through said incision, and (3) simultaneously infusing and aspirating fluid to and from said body by means of an instrument comprising:
   (a) an outer tube having a proximal end and a distal end;
   (b) an inner transfer tube housed within and concentric to said outer tube, said inner tube having a proximal end and a distal end, and having a segment extending proximally beyond the proximal end of said outer transfer tube;
   (c) a first supply tube connected to said proximal end of said outer transfer tube and having said proximally extending segment of said inner transfer tube extending through the wall of said first supply tube;
   (d) a second supply tube connected to said proximal end of said inner tube; and
   (e) an elongated, generally tubular housing, said housing contacting and supporting said tubes at the ends of said housing and substantially containing said outer transfer tube, said inner transfer tube, and said first and second supply tubes, the walls of said housing being spaced from said transfer tubes and said supply tubes substantially throughout the length of said housing to minimize heat transfer from said housing to said tubes.

9. A method according to claim 8, wherein said instrument further comprises at least one protuberance on the interior of said outer transfer tube and at least one complemental recess on the exterior of said inner transfer tube for preventing axial and radial movement of said inner transfer tube relative to said outer transfer tube.

* * * * *